United States Patent [19]
Nardella et al.

[11] Patent Number: 5,531,744
[45] Date of Patent: Jul. 2, 1996

[54] ALTERNATIVE CURRENT PATHWAYS FOR BIPOLAR SURGICAL CUTTING TOOL

[75] Inventors: Paul C. Nardella, Wareham, Mass.; David C. Yates, West Chester, Ohio; Jesse J. Kuhns, Cincinnati, Ohio; Richard P. Nuchols; Martin Madden, both of Loveland, Ohio; Steven H. Mersch, Germantown, Ohio

[73] Assignees: Medical Scientific, Inc., Taunton, Mass.; Ethicon Endo-Surgery, Cincinnati, Ohio

[21] Appl. No.: 348,038

[22] Filed: Dec. 1, 1994

Related U.S. Application Data

[63] Continuation-in-part of Ser. No. 285,413, Aug. 3, 1994, which is a continuation of Ser. No. 5,006, Jan. 15, 1993, abandoned, which is a continuation-in-part of Ser. No. 786,752, Nov. 1, 1991, abandoned.

[51] Int. Cl.$^6$ .................................................. A61B 17/36
[52] U.S. Cl. ............................... 606/48; 606/39; 606/41; 606/45; 606/142; 227/175.1; 227/180.1
[58] Field of Search ....................... 606/32–34, 37, 606/38–42, 45–50, 142, 143, 167, 170–172; 227/175.1, 180.1

[56] References Cited

U.S. PATENT DOCUMENTS

| | | |
|---|---|---|
| 1,683,708 | 9/1925 | Wappler et al. . |
| 1,881,250 | 10/1932 | Tomlinson ........................... 606/50 |
| 2,031,682 | 11/1932 | Wappler et al. . |
| 2,068,721 | 11/1932 | Wappler et al. . |
| 3,768,482 | 10/1973 | Shaw . |
| 3,826,263 | 7/1974 | Cage et al. . |
| 3,952,748 | 4/1976 | Kaliher et al. ........................... 606/34 |
| 4,038,984 | 8/1977 | Sittner . |
| 4,043,342 | 8/1977 | Morrison, Jr. ........................... 606/50 |
| 4,161,940 | 7/1979 | Does et al. . |
| 4,202,337 | 5/1980 | Hren et al. . |
| 4,228,800 | 10/1980 | Degler, Jr. et al. . |
| 4,334,539 | 6/1982 | Childs et al. ........................... 606/34 |
| 4,353,371 | 10/1982 | Cosman . |
| 4,534,347 | 8/1985 | Taylor . |
| 4,651,734 | 3/1987 | Does . |
| 4,655,216 | 4/1987 | Tischer . |
| 4,674,498 | 6/1987 | Stasz . |
| 4,712,544 | 12/1987 | Ensslin . |
| 4,784,137 | 11/1988 | Kulik et al. ........................... 606/142 |
| 4,815,465 | 3/1989 | Alvarado ........................... 606/164 |
| 4,931,047 | 6/1990 | Broadwin et al. . |
| 5,013,312 | 5/1991 | Parins et al. . |
| 5,389,098 | 2/1993 | Tsuruta et al. ........................... 606/49 |
| 5,403,312 | 4/1995 | Yates et al. ........................... 606/50 |

FOREIGN PATENT DOCUMENTS

| | | |
|---|---|---|
| 1459659 | 2/1989 | Russian Federation . |

OTHER PUBLICATIONS

New Medical Archive, First Issue (The 211th) Jan.–Feb. 1958, Vittenberger.
Vittenberger, "Instrument for Stomach Resection and Bowel Anastomosis Used During Closed Procedures", New Surgical Archive, Ministry of Health of the Ukraine Soviet Socialist Republic (Jan.–Feb. 1958).

*Primary Examiner*—Angela D. Sykes
*Assistant Examiner*—Michael Peffley
*Attorney, Agent, or Firm*—William C. Geary, III; Lahive & Cockfield

[57] ABSTRACT

A bipolar electrosurgical tool comprises a retractable cutting element movable along a cutting path and an electrical energy supply source which communicates electrical energy (e.g., radio frequency energy) through one or more energy delivering electrodes associated with a tissue affecting portion of the tool to tissue adjacent the electrodes. One or more additional electrodes, such as return electrodes, form a second pole of the bipolar electrical connection are also associated with the tissue affecting portion and are electrically isolated from the energy delivering electrode. Various combinations of electrically conductive and electrically isolated elements associated with the tissue affecting portion of the device can be used as the two poles of the bipolar system.

26 Claims, 6 Drawing Sheets

ALTERNATIVE CURRENT PATHWAYS FOR BIPOLAR SURGICAL CUTTING TOOL

This is a continuation-in-part application of application Ser. No. 08/285,413, filed on Aug. 3, 1994 which, in turn, is a continuation application of Ser. No. 08/005,006, filed on Jan. 15, 1993, now abandoned, which, in turn, is a continuation-in-part of Ser. No. 07/786,752, filed on Nov. 1, 1991, now abandoned.

BACKGROUND OF THE INVENTION

The present invention relates to an electrosurgical tool which is adapted to simultaneously cut, fuse, and cauterize the cut tissue so as to improve hemostasis and to promote healing.

Surgical procedures often require incisions to be made in internal organs, such as the intestine, causing profuse bleeding at the site of the incision. Prompt control or elimination of the bleeding is of paramount importance to the success and safety of the procedure. Hemostasis is quite important in endoscopic and laproscopic surgical procedures since failure to control bleeding could result in the need to resort to more invasive surgical techniques to stop bleeding.

Currently known surgical cutting devices utilize different techniques to control or eliminate bleeding. One known device is the Proximate Linear Cutter available from the Ethicon, Inc. of Somerville, N.J. This device is specifically adapted to make an incision in tissue or in an organ such as the intestine. The device engages a portion of the tissue or organ between two tyne-like members. To effect cutting, a blade mounted on one of the tynes travels along a predetermined path, thereby making a linear incision through the tissue or organ. Simultaneously, surgical staples are deployed by the cutting device on either side of the incision, resulting in the separation of the organ into two segments, each of which is sealed adjacent to the incision by surgical staples. Despite the use of surgical staples and the precise cutting of the tissue, bleeding is not entirely eliminated and separate cauterization procedures must often be utilized to control or stop bleeding.

Surgical devices also are known which utilize electrical current in the form of radio frequency (RF) energy to cauterize tissue and to prevent or control bleeding. U.S. Pat. No. 4,651,734 discloses a surgical scalpel modified to include an electrode. This scalpel has the ability to cut tissue and, when properly positioned, to cauterize tissue following a cutting procedure. Such a surgical tool is useful but does not simultaneously cut and cauterize tissue. The separate cauterization procedure which must be utilized is relatively time consuming and may result in unnecessary bleeding. Moreover, such a scalpel is not well suited to some surgical procedures, such as endoscopic and laproscopic procedures. The use of such a scalpel also is not practical in procedures that require the transection of the intestine.

Accordingly, there is a need for a surgical tool which conveniently and safely enables precise incisions to be made in internal organs, and which simultaneously is able to eliminate essentially all bleeding which results from the incision.

It is thus an object of the invention to provide a surgical tool which has improved cutting capability and which decreases some of the risk associated with surgery by minimizing the amount of bleeding resulting from incisions. Another object is to provide a surgical tool which is adapted to simultaneously cut tissue and to cauterize the cut tissue. It is also an object to provide such a surgical tool that optimizes the current pathways through which electrosurgical energy is delivered to tissue. A further object is to provide an electrosurgical tool which is specifically adapted to make incisions in internal organs and, simultaneously, to fuse the tissue adjacent to the incision in order to eliminate any associated bleeding. Other objects of the invention will be apparent upon reading the disclosure which follows.

SUMMARY OF THE INVENTION

The present invention comprises an electrosurgical cutting tool which is able to effect a precise incision through tissue, while at the same ensuring that essentially all of the bleeding which results from the incision is controlled or eliminated. The electrosurgical cutting tool is a bipolar device that features a housing including a proximal handle portion and a distal tissue affecting or cutting portion. The tissue affecting portion preferably includes opposed first and second members having tissue engaging surfaces. A cutting element is associated with either the first or the second member and is able to be manipulated to make an incision in tissue. Further, at least one energy delivering electrode, that serves as one pole of a bipolar system, is associated with either of the opposed tissue contacting surfaces of the members. At least one additional electrode, such as a return electrode, serves as an opposite pole of the bipolar system and is associated with one or both of the tissue contacting surfaces of the two members and is electrically isolated from the energy delivering electrode.

The electrosurgical device also includes one or more surgical staples, preferably disposed within a staple cartridge associated with one of the first or second members of the tissue affecting portion. A driver means is also provided to deploy the surgical staples to tissue. Preferably an anvil device forms the tissue engaging surface opposite the surgical staple cartridge to effect closure of the deployed surgical staples.

A feature of the electrosurgical tool of the invention is that it enables optimization of the current pathways for delivering electrosurgical energy to tissue. Accordingly, various tissue contacting components of the electrosurgical device may be used to form the two opposite poles of the bipolar electrosurgical system. Tissue contacting elements which may serve as electrodes include the cutting element, the surgical staples, driver means, the anvil, or an additional electrode-forming device associated with the tool. Elements that serve as opposite poles of the bipolar system must be electrically isolated from each other.

The electrosurgical energy delivered to tissue through one or more electrodes associated with the electrosurgical tool improves the tissue cutting ability of the device, and more importantly, facilitates cauterization and/or fusion of the tissue following the incision. Radio frequency energy is the preferred form of electrosurgical energy. The use of the tool of the present invention facilitates the simultaneous cutting of tissue, and cauterizing and fusing of tissue adjacent the incision, thus eliminating virtually all resulting bleeding.

DETAILED DESCRIPTION OF THE INVENTION

Figure 1:
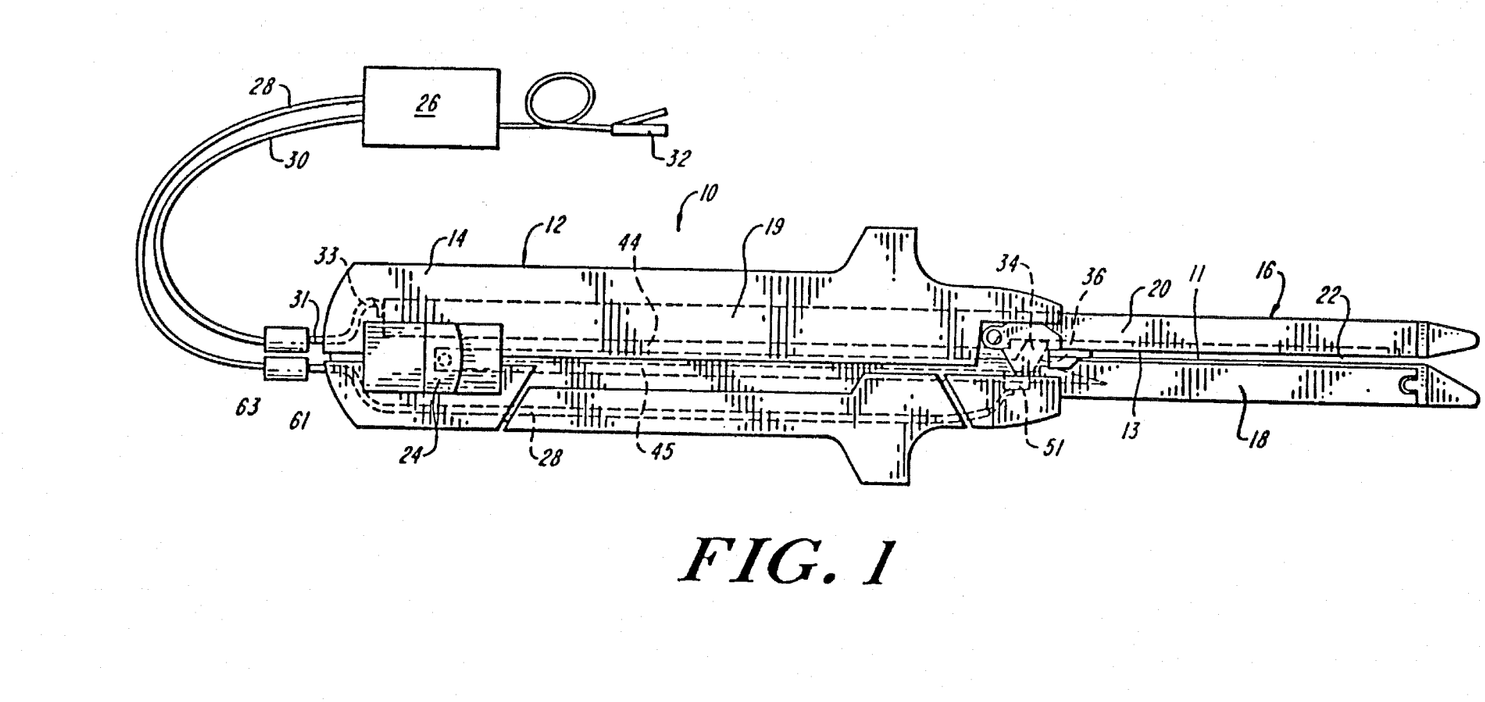
FIG. 1 schematically illustrates an electrosurgical tool according to the present invention, including a supply source of electrosurgical energy.
Figure 2:
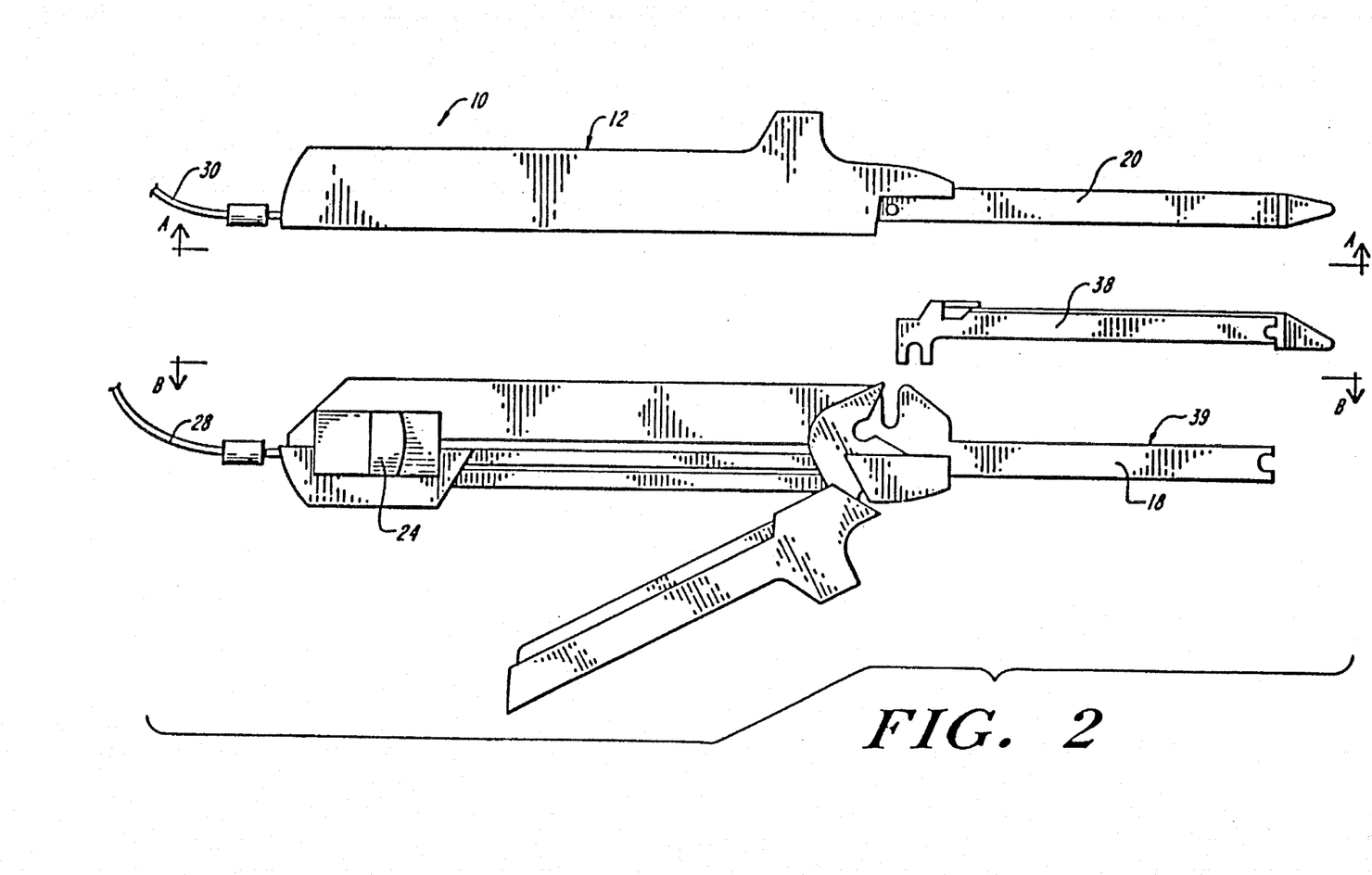
FIG. 2 is an exploded side view of the electrosurgical cutting tool illustrated in FIG. 1.

FIGS. 1 and 2 illustrate one embodiment of the invention in which the surgical cutting tool 10 comprises a housing 12 including a handle region 14. Adjacent handle region 14 is a distal, tissue affecting portion 16 which includes a first tyne 18 and a second tyne 20. First tyne 18 and second tyne 20 include first and second tissue contacting surfaces 11, 13, respectively. The two tynes 18, 20 of cutting template element 16 are substantially parallel and define a tissue engaging space 22 into which is inserted the tissue or organ to be incised. In a preferred embodiment, the surgical tool 10 includes a lever 24 which facilitates the movement of a cutting element 34 along a predetermined path.

FIG. 1 further illustrates an electrosurgical generator 26 which serves as an energy source from which electrical current, preferably in the radio frequency range, is communicated to the cutting tool through insulated wire 28. Insulated wire 30 communicates through connector 31 and internal ground wire 33 with a conductive portion of tyne 20 which serves an electrode representing one pole of a bipolar system. A control switch 32, preferably in the form of a foot pedal, may be used to control the power supplied to the cutting tool. Alternatively, a control switch may be disposed on a portion of the cutting tool such as the housing 12.

Figure 3:
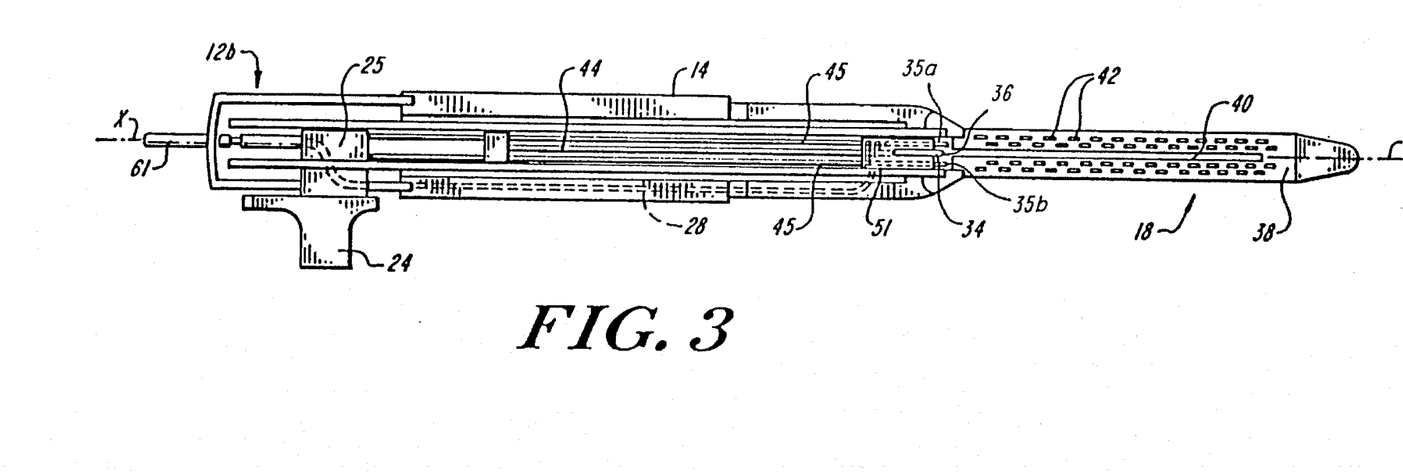
FIG. 3 is a sectional view of the electrosurgical tool of FIG. 2 at lines A—A.

As best shown in FIGS. 1 and 3, cutting element 34 can be retracted when not in use. In the retracted position cutting element 34 is disposed rearward of the first tyne 18 within a forward portion of housing 12. In one embodiment cutting element 34 is a surgical blade that includes a cutting edge 36 disposed at the leading edge of the blade. Further, a cutting element actuation arm 44 which extends into housing 12 is either attached to or integral with cutting element 34. The cutting element 34 is adapted to move along the longitudinal axis x of the tyne 18 upon actuation of lever 24 in order to effect the cutting of tissue.

Figure 6A:
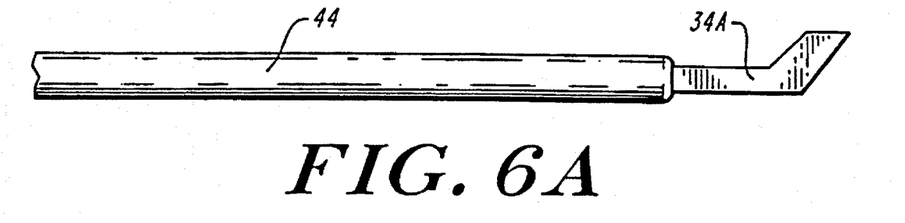
FIGS. 6A and 6B schematically illustrate alternative cutting elements applicable to the present invention.
Figure 6B:
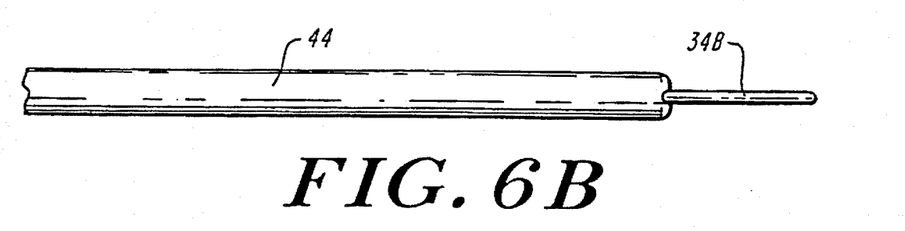

FIGS. 6A and 6B illustrate additional embodiments of the cutting element 34. Illustrated in FIG. 6A is a cutting blade 34A. The blade 34A is attached to the blade actuating arm 44 to effect movement of the blade 34A through the cutting groove 40. Blade 34A may be formed from a conductive metal, but need not have a sharpened edge. The blade 34A may also be formed of a non-conductive substrate onto which a conductive coating is applied. The substrate can be composed of a non-conductive, non-sharpened material, such as a non-conductive metal, plastic or ceramic, which is coated with a conductive material, for example, a conductive metal or conductive non-metals such as suitable polymers or ceramics. As noted, blade 34A need not be sharpened.

FIG. 6B depicts another embodiment of the cutting element 34 in which an electrode wire 34B is operatively associated with the blade actuating arm 44. Electrosurgical energy can be communicated to the wire 34B directly from wire 28 or through conductive bushing 51. Once electrical current is supplied to the wire 34B, and the actuating arm 44 and wire 34B are actuated, the wire 34B simultaneously cuts and cauterizes the biological tissue located within the tissue engaging space 22. The wire 34B can be constructed of a variety of materials known to those of ordinary skill in the art. Typically, wire 34A has a conductive core wrapped in an insulating sheath.

A surgical staple cartridge 38 may optionally be seated within the first tyne 18, as illustrated in FIGS. 1 through 3. Cartridge 38 is adapted to securely fit within a channel 39 formed in tyne 18. The staple cartridge 38 includes a central cutting groove 40 through which the cutting element 34 passes during a cutting procedure. Dual rows of openings 42 through which surgical staples (not shown) may emerge straddle either side of groove 40, which extends parallel to the longitudinal axis x of the tyne 18.

As further illustrated in FIGS. 1 and 3, lever 24 preferably is connected to the cutting element 34 through an actuation arm 44. Forward movement of lever 24 thus effects movement of the cutting element 34 causing it to traverse the cutting groove 40. Preferably, a staple ejecting mechanism, such as driver mechanism 45, is actuated simultaneous with actuation of the cutting element. In this way staples are ejected through openings 42 as the blade traverses the groove 40. Preferably the driver mechanism 45 includes left and right drive elements 35a, 35b.

Figure 5:
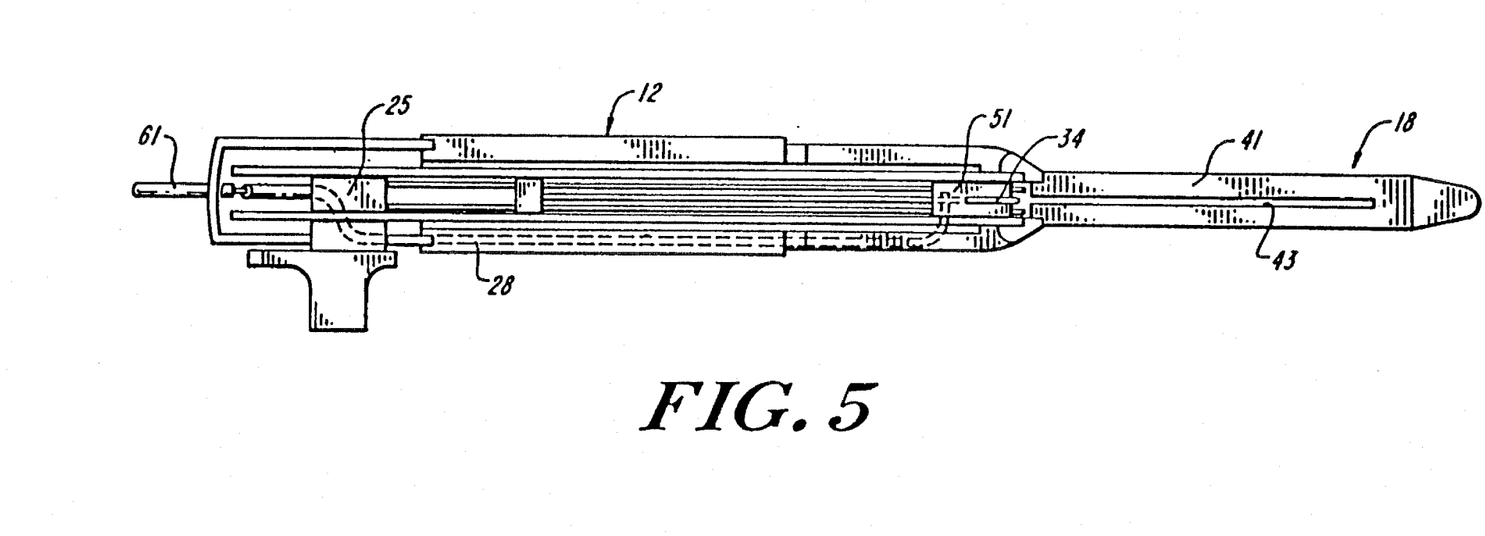
FIG. 5 is a sectional view of the electrosurgical tool of FIG. 2 at lines B—B in an embodiment which does not include a surgical staple cartridge.

FIG. 5 illustrates an embodiment of the invention in which the electrosurgical cutting tool does not utilize surgical staples. In this embodiment the tissue contacting surface 41 of tyne 18 is constructed of or coated with a non-conducting material, such as a suitable polymer. Surface 41 defines a cutting groove 43 through which cutting element 34 travels when it effects a cutting procedure.

Figure 4:
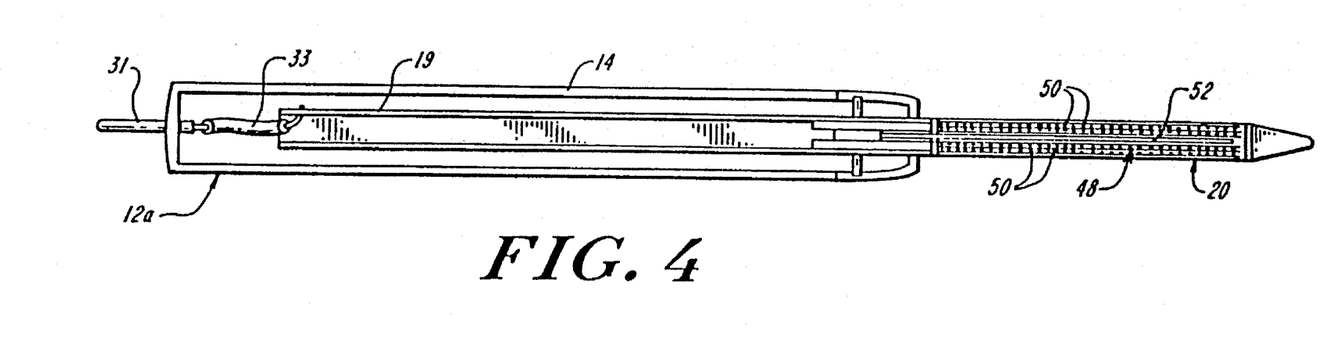
FIG. 4 is a sectional view of the electrosurgical tool of FIG. 2, at lines B—B.

As shown in FIG. 4, tyne 20 is secured within housing segment 12a which preferably is detachable from housing segment 12b associated with tyne 18. Further, tyne 20 has a tissue-contacting surface 48 which faces first tyne 18. A central groove 52 is formed in surface 48, superimposable with cutting grooves 40 or 43 of tyne 18, to facilitate movement of the cutting element along longitudinal axis x.

In an embodiment in which surgical staples are to be deployed simultaneously with a cutting procedure, staple cartridge 38 is present within tyne 18. In addition, surface 48 of tyne 20 includes an anvil with a plurality staple-closing depressions 50 which correspond to the openings 42 in staple cartridge 38. Preferably, dual rows of depressions are disposed on either side of groove 52. In an embodiment in which a staple cartridge is not utilized, the surface 48 may be substantially smooth and absent depressions 50. In either embodiment, however, surface 48 of tyne 20 should be made of a conductive material so that it may serve as a return electrode for electrical energy delivered through the cutting blade.

In some instances, it may be desirable to apply electrosurgical energy through the surgical staples as well as through blade 34. One skilled in the art could easily modify the electrosurgical tool described herein by connecting internal wire 28 to the driver mechanism 45, and/or to driver elements 35a, 35b, as well as to the cutting element 34.

FIGS. 1 through 5 illustrate the connection of the cutting tool 10 to electrosurgical generator 26. As illustrated, an inner wire 28 extends between conductive bushing 51 and electrical connector 61 which protrudes from housing 12.

Insulated wire 28 may be attached to electrical connector 61 through connector 63. Bushing 51 communicates electrical current from the generator 26 to cutting element 34, directly or through blade actuation arm 44. In a preferred embodiment arm 44 and cutting element 34 are able to slide within bushing 51 while maintaining electrical contact therewith.

In one embodiment, the electrosurgical cutting tool 10 of the invention comprises a bipolar cutting tool in which the cutting element 34 is electrically isolated from the remainder of the tool and serves as an electrode to deliver electrosurgical energy to the tissue. In this embodiment tyne 20 serves as the return or ground electrode. In other embodiments, it is possible that the surgical tool may comprise a monopolar tool in which electrosurgical energy is delivered through the cutting element 34, and a separate ground plate (not shown) serves as the return electrode.

In one bipolar mode surface 48 of tyne 20 serves as a second pole of the bipolar system, and can be an energy delivering electrode or a return electrode. Accordingly, exterior ground wire 30 communicates with internal ground wire 33 through connector 31. Internal ground wire 33, in turn, is in electrical communication with a conductive internal anchoring component 19 of tyne 20. Where the cutting device is used in the monopolar mode, external ground wire 30 should not communicate with tyne 20, and the tissue contacting surface 48 of tyne 20 should be made from or coated with a non-conductive material.

Figure 7:
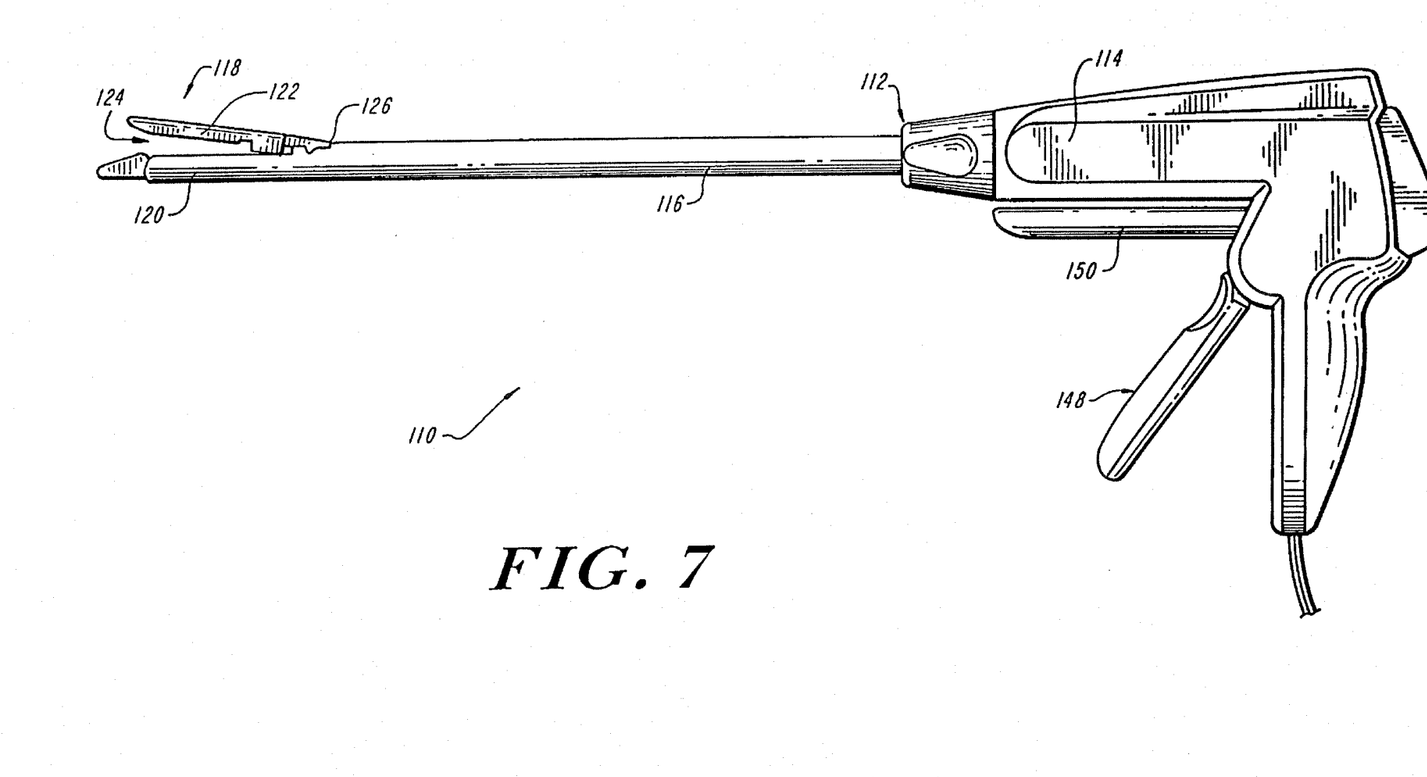
FIG. 7 is a side view of an alternative electrosurgical tool constructed according to the present invention.
Figure 8:
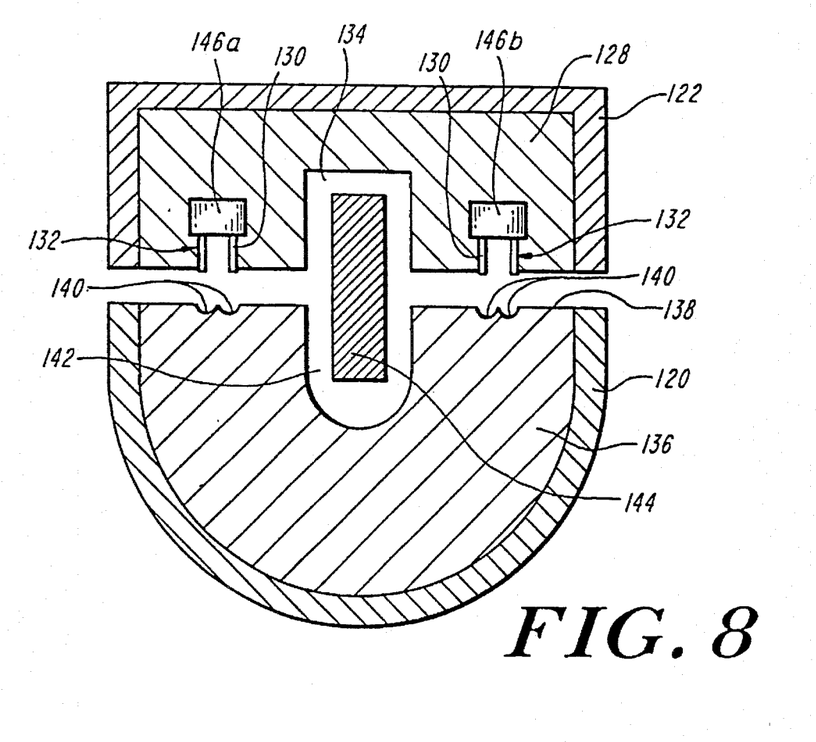
FIG. 8 is a schematic, front view of an electrosurgical tool according to the present invention.

FIGS. 7 and 8 illustrate another embodiment of a bipolar electrosurgical tool 110 constructed according to the present invention. As illustrated in FIG. 7, tool 110 includes a housing 112, a proximal handle portion 114, elongate member 116 extending from the handle region, and a tissue affecting portion 118. The tissue affecting portion 118 includes first and second tynes, 120, 122 that define a tissue engaging space 124 therebetween. One tyne, preferably tyne 120, is integral with member 116 while the other tyne, such as tyne 122, is able to articulate in a jaw-like manner. Tyne 122 can be pivotally attached to member 116 at pivot point 126.

Additional features and components that can be present within a tissue affecting portion 118 are illustrated in FIG. 8. The tissue affecting portion 118 can include a surgical staple housing cartridge 128 mounted within one of the tynes, such as tyne 122. Cartridge 128, which is similar to cartridge 38 of tool 10, houses a plurality of surgical staples 130 that are oriented in adjacent rows 132. Preferably, two rows 132 of staples 130 are disposed on either side of the central, longitudinally extending groove 134 formed within cartridge 128. Each staple 130 is preferably oriented to be parallel with the longitudinal axis of the tynes 120, 122. The opposed tyne, such as tyne 120, includes an anvil 136 having disposed on its tissue contacting surface 138 a number of depressions 140 that effect closure of deployed surgical staples. Anvil 136 also has a central, longitudinally extending groove 142 formed therein that is superimposable on groove 134.

A cutting element 144 is associated with the tissue affecting portion and is adapted to be moved along the longitudinal axis of the tissue affecting portion 118 within grooves 134, 142. Cutting element 144 can be of similar construction to cutting element 34 described above. FIG. 8 also illustrates that left and right drivers 146a, 146b are associated with tyne 122 of tissue affecting portion 118. Driver elements 146a, 146b preferably are actuated, substantially simultaneous with the cutting element, to move in a direction parallel to cutting element 144. As drivers 146 move through cartridge 128 they cause staples 130 to be deployed to tissue in the manner described above with respect to the electrosurgical tool 10 illustrated in FIGS. 1 through 5.

Electrosurgical tool 110 can have electrical connections similar to those described above with respect to electrosurgical tool 10 illustrated in FIGS. 1 through 5.

The bipolar electrosurgical tool of the invention can be designed and constructed to improve the efficacy of surgical procedures by optimizing the current pathways through which bipolar electrosurgical energy is delivered to tissue. That is, various conductive elements within the tissue affecting portion can serve as the two opposite poles of a bipolar electrosurgical tool. The conductive elements of the tissue affecting portion of the electrosurgical tool of the invention include the anvil, cutting element and left and right drivers. Obviously, elements that are used as opposite poles in the bipolar system should be electrically isolated from each other. Depending upon the overall construction of an electrosurgical tool, and the surgical procedures the tool is intended for, different current pathways may be chosen to achieve what is perceived to be the best current pathway.

Table 1, shown below, graphically illustrates the various combinations of current pathways that can be achieved using different combinations of electrodes.

TABLE 1

| | Possible Current Pathways Conductive Element | | |
|---|---|---|---|
| Anvil | Cutting Element | Left Driver | Right Driver |
| 1 | 2 | N | N |
| 1 | N | 2 | 2 |
| 1 | N | 2 | 1 |
| 1 | N | 1 | 2 |
| N | 1 | 2 | 2 |
| N | 1 | 2 | 1 |
| N | 1 | 1 | 2 |
| 1 | 2 | 1 | 1 |
| 1 | 2 | 2 | 1 |
| 1 | 2 | 1 | 2 |
| 1 | 2 | 2 | 2 |
| N | N | 1 | 2 |

In Table 1 the numerals "1" and "2" denote opposite poles of the bipolar system and either of the poles may function as an energy delivering electrode or as a return electrode. The notation "N" denotes an element that is not used as either pole of the bipolar electrosurgical system.

It is understood that the combinations identified in Table 1 are exemplary and that other combinations are possible as well. Further, other conductive elements may be incorporated into the tissue affecting portion to serve as a pole of the bipolar system.

Preferred configurations include those in which the anvil is used as a one pole and both the left and right drivers are used as opposite poles while the cutting element does not participate as an electrode. Another preferred configuration uses the cutting element as one pole and the left and right drivers as the opposite pole. In this embodiment the anvil is not used as an electrode. In another preferred configuration the anvil is used as one electrode while the cutting element and the left and right drivers are all used as opposite poles of the electrosurgical system.

As noted above, generator 26 supplies electrosurgical energy to the energy delivering electrode(s) of tools 10, 110. Virtually any generator which provides electrosurgical energy for medical applications may be used with the present invention. Preferably, the generator is a voltage determinative, low source impedance generator which provides radio frequency energy. Preferably, a suitable generator can supply up to 2 amps of current and has a source impedance value of less than 10 ohms.

The energy supplied by generator 26 to the electrosurgical cutting device is preferably in the radio frequency range. Although virtually any frequency in the RF range may be supplied to the cutting device, the preferred frequency range is about 100 KHz to about 1000 KHz.

The energy requirements of the electrosurgical tool of the present invention are dynamic and depend to a great extent upon the impedance values of the tissue encountered by the blade during cutting procedures. The impedance of tissue varies among tissue types and the amount of blood and/or fluid present in or around the tissue. The amount of current delivered by the tool to the tissue is a function of the impedance of the tissue. Where tissue contacted has a lower impedance value, more current will be delivered to the tissue by the blade, and, conversely, less current will be delivered to tissue having a higher impedance value. Generally, the amount of current delivered to tissue ranges between about 0.5 and 2.0 amps. The voltage applied to the tissue between the blade and the return electrode typically is between about 50 to 100 volts rms.

The surgical tool of the present invention is particularly well adapted for use in surgical procedures which require transection of an organ such as the intestine. In operation, the tissue (e.g., intestine) is placed within space 22 or 124 defined by tynes 18 and 20, or by tynes 120, 122 The cutting element is moved forward along the longitudinal axis x of tynes 18 and 20 by movement of lever 24. In the embodiment illustrated in FIG. 8, tissue (not shown) is compressed between tynes 120, 122 by actuating lever 148 on the handle region 114 of tool 110. Thereafter, cutting element is actuated by manipulating lever 150. As the cutting element moves forward, it passes through the tissue causing it to be severed. Simultaneously, electrical energy (e.g., radio frequency energy), is delivered to tool 10 by activating, for example, foot switch 32. Alternatively, electrosurgical energy can be delivered to the tool by activating a switch mounted on the handle of tool, such as switch 152 of tool 110. The electrosurgical current is communicated from the energy delivering electrode(s) to the tissue adjacent and in the vicinity of the electrode(s).

During a cutting procedure the cutting element should be actuated such that it requires approximately 1.5 to 4.5 seconds to move along its predetermined path to sever tissue. Current should be delivered through the energy delivering electrode(s) to the tissue during the entire cutting procedure.

The application of electrical energy in this manner provides two advantages. Electrosurgical energy is delivered through the energy delivering electrodes to adjacent tissue to allow for more effective cutting action (in an embodiment in which the cutting element delivers electrosurgical energy) and to promote cauterization and/or tissue fusion which effectively eliminates all or substantially all bleeding which results from the incision. The cauterization and/or fusion effect imparted to tissue minimizes blood loss and increases the safety of the surgical procedure as cauterization occurs at substantially the same time that the incision is made.

One skilled in the art will appreciate that a variety of materials are well suited for the manufacture of the electrosurgical tool of this invention. For example, housing 12 and cartridge 38 may be made from or coated with various non-conducting polymers. The conductive components of the tool may be made of various metals, including surgical grade stainless steel and aluminum.

Although the invention is described with respect to the cutting tool illustrated in FIGS. 1 through 8, it is understood that various modifications may be made to the illustrated electrosurgical cutting device without departing from the scope of the invention. For example, a variety of blade actuation mechanisms may be used. Also, it is not necessary that tynes 18, 20, 120, and 122 take on the shape and orientation illustrated in the drawings. Moreover, the electrical connection between the generator may be made in ways other than those illustrated and described herein. The invention is also able to be used in connection with circular stapling devices, such as described in U.S. Pat. No. 5,104,025, which is fully incorporated by reference herein.

Further, the use of alternative electrosurgical current pathways is not limited to an electrosurgical tool of the types shown in FIGS. 7 and 8. This aspect of the invention is applicable to a tool such as tool 10 illustrated in FIGS. 1–5, as well as to other electrosurgical tools of numerous shapes and sizes.

Various improvements and modifications may be made to this invention without departing from its intended scope.

What is claimed is:

1. A bipolar electrosurgical device, comprising:

a proximal handle region;

a distal, tissue affecting portion adjacent to the handle portion, the tissue affecting portion including opposed first and second tissue engaging surfaces;

a cutting element disposed within one of the first or second tissue engaging surfaces, the cutting element including at least one first electrode serving as a first pole of a bipolar system;

at least one second electrode disposed within the first and/or second tissue engaging surfaces, the second electrode being electrically isolated from the first electrode and serving as an opposite pole of the bipolar system;

one or more surgical staples disposed within one of the first or second tissue engaging surfaces of the tissue affecting portion;

a driver means, disposed adjacent the surgical staples, for deploying the surgical staples;

anvil means for effecting closure of one or more of the surgical staples, the anvil means being disposed within one of the first or second tissue engaging surfaces opposite the surgical staples; and electrosurgical current delivery means, disposed within the electrosurgical device, for communicating electrical energy through the energy delivering electrode to tissue to effect cutting and/or cauterization of tissue.

2. The device of claim 1 further comprising actuation means for manipulation the cutting element to sever tissue.

3. The device of claim 2 wherein the cutting element is a cutting blade.

4. The device of claim 1 wherein the surgical staples are present in one or more staple cartridges, the surgical staples being adapted to deploy at least one row of surgical staples on either side of a longitudinal midline of the tissue affecting portion, with each surgical staple being oriented parallel to the longitudinal midline.

5. The device of claim 4 wherein the anvil means serves as the second electrode, and is one of an additional energy delivering electrode or a return electrode.

6. The device of claim 4 wherein the driver means comprises a right driver element and a left driver element and wherein each row of surgical staples is deployed by a corresponding driver element.

7. The device of claim 6 wherein right and left driver elements are disposed on opposite sides of the longitudinal midline and are electrically isolated from each other.

8. The device of claim 7 wherein the first and second driver elements are electrodes that are opposite poles of the bipolar system.

9. The device of claim 7 wherein one of the right or left driver elements serve as the second electrode and the right or left driver elements are each either an energy delivering electrode or a return electrode, and the other of the right or left driver elements serves as an additional first electrode.

10. The device of claim 9 wherein the anvil means serves as an additional electrode and is one of an energy delivering electrode or a return electrode.

11. The device of claim 6 wherein the anvil means serves as an additional second electrode and is one of an energy delivering or a return electrode.

12. The device of claim 1 wherein the first electrode associated with the cutting element is one of an energy delivering electrode or a return electrode.

13. The device of claim 1 wherein the cutting element is one of the energy delivering electrode or the return electrode.

14. The device of claim 1 wherein the driver means serves as the second electrode and is one of an energy delivering electrode or a return electrode.

15. The device of claim 14 wherein the anvil means serves as an additional second electrode which forms the same pole of a bipolar system as the driver means.

16. The device of claim 15 wherein the anvil means serves as an additional second electrode which forms an opposite pole of a bipolar system as do the cutting element and the driver means.

17. A bipolar electrosurgical device, comprising:

a proximal handle region;

a distal, tissue affecting portion including opposed first and second tissue engaging surfaces;

a cutting element disposed on one of the first or second tissue engaging surfaces;

one or more surgical staples associated with one of the first or second tissue engaging surfaces of the tissue affecting portion;

a driver means for deploying the surgical staples;

anvil means for effecting closure of one or more of the surgical staples, the anvil means being associated with one of the first or second tissue engaging surfaces opposite the surgical staples, the anvil means further including at least one first electrode serving as the first pole of a bipolar system;

at least one second electrode associated with a tissue contacting portion of the driver means, the second electrode being electrically isolated from the first electrode and serving as an opposite pole of the bipolar system; and electrosurgical current delivery means for communicating electrical energy through the energy delivering electrode to tissue to effect cutting and/or cauterization of tissue.

18. The device of claim 17 wherein the first electrode is either an energy delivering electrode or a return electrode.

19. The device of claim 17 wherein the second electrode is disposed on the driver means and is either an energy delivering electrode or a return electrode.

20. The device of claim 17 wherein the surgical staples are present in one or more staple cartridges, the surgical staples being adapted to deploy at least one row of surgical staples on either side of a longitudinal midline of the tissue affecting portion, with each surgical staple being oriented parallel to the longitudinal midline.

21. The device of claim 20 wherein the driver means comprises a right driver element and a left driver element and wherein each row of surgical staples is deployed by a corresponding driver element.

22. The device of claim 21 wherein right and left driver elements are disposed on opposite sides of the longitudinal midline and are electrically isolated from each other.

23. The device of claim 22 wherein the right and left driver elements serve as opposite poles of a bipolar system, and each can be one of an energy delivering electrode or a return electrode.

24. A bipolar electrosurgical device, comprising:

a proximal handle region;

a distal, tissue affecting portion including opposed first and second tissue engaging surfaces;

a cutting element disposed on one of the first or second tissue engaging surfaces;

one or more surgical staples associated with one of the first or second tissue engaging surfaces of the tissue affecting portion, the surgical staples being present in one or more staple cartridges and being oriented, such that at least one row of surgical staples is deployed on either side of a longitudinal midline of the tissue affecting portion;

right and left driver means for deploying the surgical staples, the right and left driver means each being disposed on opposite sides of the longitudinal midline and being electrically isolated from each other;

anvil means for effecting closure of one or more of the surgical staples, the anvil means being associated with one of the first or second tissue engaging surfaces opposite the surgical staples, the anvil means further including at least one first electrode serving as the first pole of a bipolar system;

at least one second electrode associated with one of the right or left driver means, the second electrode being electrically isolated from the first electrode and serving as an opposite pole of the bipolar system; and electrosurgical current delivery means for communicating electrical energy through the energy delivering electrode to tissue to effect cutting and/or cauterization of tissue.

25. The device of claim 24 wherein the right and left driver means serve as opposite poles of a bipolar system, and each can be one of an energy delivering electrode or a return electrode.

26. A bipolar electrosurgical device, comprising:

a proximal handle region;

a distal, tissue affecting portion adjacent to the handle portion, the tissue affecting portion including opposed first and second tissue engaging surfaces;

a cutting element disposed within one of the first or second tissue engaging surfaces;

one or more surgical staples disposed within one of the first or second tissue engaging surfaces of the tissue affecting portion;

a driver means for deploying the surgical staples, the driver means comprising right and left driver elements disposed adjacent the surgical staples and on opposite sides of a longitudinal midline of the tissue affecting portion and being electrically isolated from each other;

a first electrode serving as a first pole of a bipolar system, the first electrode being in electrical communication with one of the left or right driver elements and being an energy delivering electrode or a return electrode;

at least one second electrode being in electrical communication with the other of the left or right driver elements, the second electrode being electrically isolated from the first electrode and serving as an opposite pole of the bipolar system;

anvil means for effecting closure of one or more of the surgical staples, the anvil means being disposed within one of the first or second tissue engaging surfaces opposite the surgical staples; and electrosurgical current delivery means, disposed within the device, for communicating electrical energy through the energy delivering electrode to tissue to effect cutting and/or cauterization of tissue.

* * * * *